United States Patent [19]

Reyner

[11] Patent Number: 4,696,294
[45] Date of Patent: Sep. 29, 1987

[54] CONTRACEPTIVE DEVICE AND RELATED METHOD
[76] Inventor: Franklin C. Reyner, 165 N. Village Ave., Rockville Center, N.Y. 11570
[21] Appl. No.: 298,209
[22] Filed: Aug. 31, 1981
[51] Int. Cl.$^4$ ................................................. A61F 5/46
[52] U.S. Cl. ..................................................... 128/131
[58] Field of Search ........................ 128/127, 130, 131
[56] References Cited
U.S. PATENT DOCUMENTS
D. 246,119 10/1977 Okamoto ..................... 128/132 R
3,536,066 10/1970 Ludwig ........................ 128/132 R
4,198,965 4/1980 Strickman et al. ................... 128/127

Primary Examiner—Deborah L. Kyle
Assistant Examiner—Thomas J. Wallen
Attorney, Agent, or Firm—Roberts, Spiecens & Cohen

[57] ABSTRACT

The outer convex surface of a contraceptive diaphragm is texturized in omnidirectional manner to simulate the ruggae of the vagina. The texturization takes various forms including concentric rings which can be regular or irregular or symmetrical arrangements of discrete projections.

22 Claims, 7 Drawing Figures

CONTRACEPTIVE DEVICE AND RELATED METHOD

FIELD OF INVENTION

The present invention relates to contraceptive devices and more particularly to contraceptive devices which are insertable into the vagina to block the cervical os for purposes of birth control and the like.

BACKGROUND

Contraceptive devices such as pessaries and diaphragms are known which are intended to remain in the vagina to block the cervical os and to occupy a position so as to remain substantially undisturbed within the vaginal cavity during sexual intercourse. Such devices should be soft and flexible in order to conform perfectly to the conformation of the vagina and to result in minimal awareness during wear and during coitus.

Various patents are directed to improvements in construction of pessaries and other such vaginal contraceptives. Two such patents are U.S. Pat. Nos. 2,851,032 and 4,198,976. U.S. Pat. No. 2,681,261 is also directed to a pessary, but of a significantly different type.

U.S. Pat. No. 2,851,032 (J. T. Friedman) discloses a pessary which is stabilized and non-shifting and is adapted to engage and deflect portions of the Fallopian tubes to ensure perfected results. This patent discloses an invention having for its objects the effective sealing of the cervix which is automatically self-adjusting for anterior and posterior positions of the uterus, as well as automatic provision for adjustment of lateral deflection of the uterus, as well as for prolapsed uterus or dropped womb. In achieving its objectives, this invention proposes a thin flexible diaphragm with an annular ring encircling the same, there being provided a depression in the posterior segment of the diaphragm and a pair of arched resilient transverse members in the diaphragm, these members being located parallel to each other with the depression being located therebetween.

James Drobish in U.S. Pat. No. 4,198,976 provides for reinforced devices which can be retained in the vagina during intercourse to deliver spermicidal surfactants and provide contraceptive benefits. In accordance with the Drobish invention a container is provided having walls which allow the passage of spermicidal surfactant monomers from within the container into the vagina. The configuration of the devices allows them to be placed in the closest possible proximity to the cervical os and this feature contributes to the contraceptive efficacy. The constructions such as to substantially surround and cap the cervical os. The structure comprises a dish-shaped back forming a reservoir and constituting a vaginal retaining means, the back being characterized by one or more thickened reinforced areas. A front face is provided capping the back to form a container with the front face constituting a transport surface which is made of a semi-permeable membrane describing the walls of the container. The container contains a spermicide which consists of an aqueous solution of a micelle-forming spermicidal surfactant compound of a concentration at or above the critical micelle concentration of the said surfactant compound. The reinforcing ribs may converge to the center of the back of the device to provide channels which direct the flow of spermicide towards the central portion of the transport surface.

SUMMARY OF INVENTION

Although the aforegoing inventions may be useful for the purposes intended, they are not directed towards the object of the invention which is to make more natural and satisfactory the feel of coitus to the male participant.

It is a further object of the invention to provide an improved construction for pessaries, diaphragms and the like.

It is yet another object of the invention to provide an improved method for the provision of improved diaphragms, pessaries and the like to encourage the utilization of such devices as contraceptive techniques.

Still another object of the invention is to provide improved contraceptive device constructions which are omnidirectional while achieving the aforegoing benefits.

In achieving the above and other objects of the invention, there is provided a contraceptive device comprising a flexible wall having a shape adapted for accommodation in a vaginal cavity and for capping the cervical os in the cavity, said wall having at least a generally convex outer surface, at least part of said surface having a texture therein.

Preferably the wall has a central axis and the texture is formed at least generally symmetrically about said central axis in a polar sense. The texture is moreover, according to a preferred embodiment of the invention, formed of an at least generally concentric and circular set of ridges or the like. These ridges may be formed solely in the outer surface or alternatively may be formed through the wall, whereby the ridges are formed both in the inner and outer surfaces of the device.

In accordance with conventional constructions, the device may be provided with a resilient annular ring encircling and connected to the domed wall. The ridges may be of uniform width and height or may be of irregular width and height. The height may preferably vary within a range of from about ½ to 2½ mm. The width may also vary preferably within a range of from about ½ to 2½ mm.

In accordance with one embodiment of the invention, the ridges are spaced circles. According to another embodiment, the ridges may be continuous or, still further, these ridges may be discontinuous. The texture may be formed alternatively of discrete projections. These projections may, for example, be conical in shape.

The method of the invention comprises improving the utility of a contraceptive diaphragm having an outer convex surface by texturizing the surface. It may be textured, as noted above, symmetrically in a polar sense.

Other objects, features and advantages of the invention will be found in the following detailed description as illustrated in the accompanying drawing.

DETAILED DESCRIPTION

A principle purpose of the contraceptive device is to make more natural the "feel" of the coitus to the male participant. Basically, the improvement of the invention involves a texturization of a diaphragm dome to simulate the textured surface of the vaginal mucosa. This improvement can be applied to any contraceptive diaphragm whether it be a mensinga, matrisalus arcing, flexing, flat-spring, coil-spring, or no-spring design.

The diaphragm dome, in accordance with the invention, is textured in a fashion (during its manufacture) to simulate the natural surface of the vaginal mucosa. The texturization is in the form of ridges and rugae in a pattern of variable design based upon the naturally occurring rugal pattern or in a more regular pattern. It differs from the natural pattern in that it is "omnidirectional" as will be explained hereinafter.

The usual outer diaphragm surface is smooth. This blocks off the entire anterior wall and a portion of both lateral walls of the vagina. The perception of this smooth surface to the male penis diminishes considerably the stimulating feeling of the normal natural vaginal surface and both diminishes and detracts from the effected sensual pleasure of intercourse.

The novel device of the invention eliminates the artificial surface which characterizes all current manufactured diaphragms and presents a surface simulating the normal vaginal mucosa. The enhanced stimulation eliminates the objection that most coital couples have to the feel of a diaphragm and would encourage more couples to accept the diaphragm as a contraceptive method.

The well known medical text in Gray's Anatomy states that the inner surface of the vagina is characterized by two longitudinal ridges, one on its anterior and one on its posterior wall. These ridges are called the "columns of the vagina" and from them numerous transverse ridges or rugae extend outward on either side. These rugae are divided by furrows of variable depth giving to the mucous membrane the appearance of being studded over with conical projections or papillae. These are more numerous near the orifice of the vagina.

Figure 1:
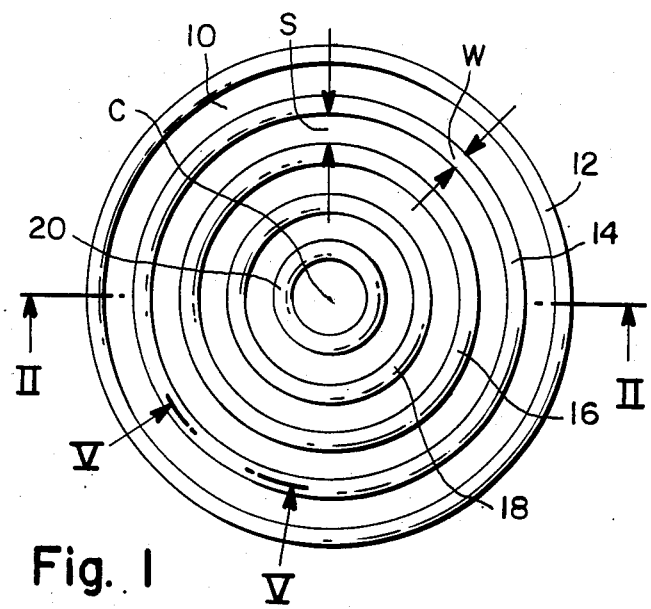
FIG. 1 is a top plan view of embodiment of the invention relating to a texturized diaphragm.
Figure 2:
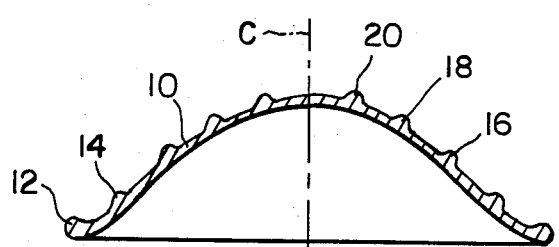
FIG. 2 is a sectional view along line II—II of FIG. 1.

Referring next to FIGS. 1 and 2, there is found therein a vaginal diaphragm consisting of a domed wall 10 encircled by a rim 12 of generally known configuration and inclusive of the variations set forth hereinabove. The construction and material for the domed wall and the rim are well known and do not require further description in this text. The texture referred to hereinafter in accordance with the invention is of the same material and preferably may be integral and therefor monolithic therewith.

In accordance with a first embodiment of the invention, there are provided a concentric series of protruding ridges indicated, for example, at 14, 16 and 18. These ridges, as well as a further ridge 20, are shown by way of example only and may be greater or lesser in number and may be evenly spaced or irregularly spaced and may be spaced, for example, at a distance S which varies between $\frac{1}{2}$ to 10 mm or more. The width of such ridges is indicated at W which may vary, for example, between $1\frac{1}{2}$ and $2\frac{1}{2}$ mm, although this range limitation may be exceeded within the scope of the invention.

The diaphragm has a center or central axis indicated at C and the ridges are preferably arranged at least generally symmetrically about this center in a polar sense. The ridges may furthermore be elliptical or polygonal and other shapes may be adapted, but preferably the general idea of retaining symmetry about the central axis should be followed in order that the device can be inserted at any polar angle whatsoever without losing the benefits of the invention.

Figure 3:
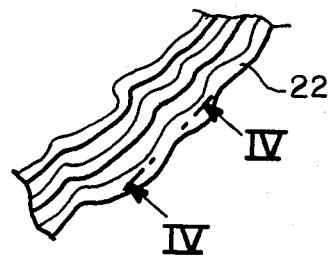
FIG. 3 is a diagrammatic fragmentary illustration of a variation of the embodiment of FIGS. 1 and 2.

FIG. 3 illustrates another embodiment of the invention whereby the ridges are irregular compared to the regular sense of the ridges illustrated in FIGS. 1 and 2. The ridges of FIG. 3 more nearly simulate the ridges or rugae of the vagina as has been discussed hereinabove.

Figure 4:
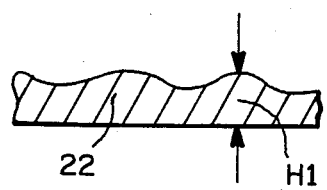
FIG. 4 is a cross-sectional view along line IV—IV of FIG. 3.

FIG. 4 illustrates a sectional along line IV—IV of FIG. 3 and illustrates that the ridges, such as indicated at 22, may be irregular in height H1 in the longitudinal sense. In other words, the ridges may follow a serpentine or irregular path rather than a linear or circular path and the height thereof may vary along the length of the same.

Figure 5:
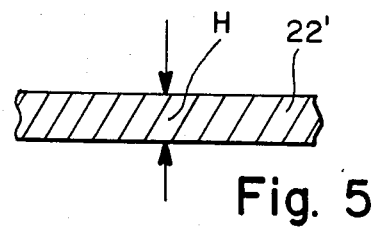
FIG. 5 is a cross-sectional view corresponding to FIG. 4 showing a further embodiment of the invention.

FIG. 5 illustrates that the ridges may be constant in height H, a ridge 22' being indicated by way of example. Such ridge may conform to the pattern indicated in FIGS. 1 and 2 or may conform to the pattern illustrated in FIG. 3 or to any other pattern providing a texturization in the outer surface of the diaphragm, such as to improve the feel of coitus to the male participant, since the wall of the vagina is more nearly simulated than in the smooth surface dome of the conventional type of diaphragm. It will again be noted that the arrangement of the ridges at least generally symmetrically about the center of the domed wall provides an omnidirectional type of diaphragm, the ridges thereby extending transverse to the longitudinal extent of the vagina and more nearly simulating the ridges or rugae in the vagina being transverse to the penetrating penis of the male participant.

Figure 6:
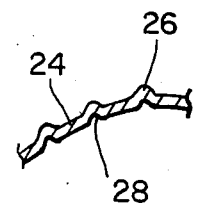
FIG. 6 shows a variation of FIG. 2 constituting still another embodiment of the invention.

FIG. 6 illustrates still a further embodiment of the invention showing a variation of FIG. 2, wherein a wall 24 similar in shape to the domed wall 10, illustrated in FIGS. 1 and 2, is provided with ridges 26, these extending completely through the wall and thereby providing grooves 28 on the inside surface of the wall as illustrated. In all other respects, the embodiment of FIG. 6 may conform with the embodiments previously described as to shape and disposition and width and height ranges.

Figure 7:
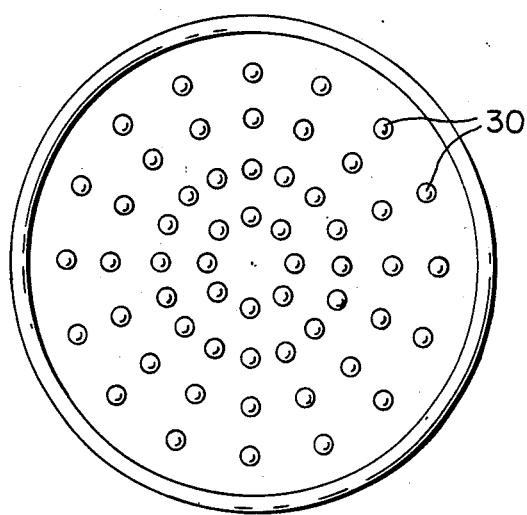
FIG. 7 illustrates still a further embodiment of the invention.

FIG. 7 illustrates still a further embodiment of the invention wherein the ridges are replaced by discrete projections, such as indicated at 30. These discrete projections will be arranged along imaginary circles or the like providing once again for a symmetrical distribution about the center of the device in a polar sense so as to provide transverse ridges or the equivalent thereof in the manner described and discussed hereinabove. These discrete projections may, for example, be generally conical in shape although they may be hemispherical or have variously shaped conformations or the like.

The invention further relates to the manufacture of devices of the aforegoing type. Manufacture of the device of the invention approximates the manufacture of currently made diaphragms. The pressure mold method usually used can be utilized along with a texturized mold for the dome in place of the presently used smooth mold. No effort need be made to alter the rim whether it contains a spring (flat or coil or flex or arching) or no spring. The insertion process for use would be the same as for smooth diaphragms whether it be manual for arching and flexing diaphragms or with an inserter in the case of coil or flat or no-spring diaphragms. Other methods of manufacture can be utilized as long as the dome is texturized. Such methods may include, for example, blow molding and injection molding techniques.

From what has been stated above, it will now appear that the invention provides a contraceptive device which comprises a flexible wall having a shape adapted for accommodation in a vaginal cavity and for capping the cervical os in said cavity, said wall having an at least generally convex outer surface, at least part of said surface having a texture of the type noted hereinabove and particularly of the type having an at least generally symmetrical arrangement about the center of the device in a polar sense. It will also be understood that the invention proposes a method which improves the utility of a contraceptive diaphragm having an outer convex surface by means of texturing the surface in the manner indicated.

There will now be obvious to those skilled in the art, many modifications and variations of the construction and method set forth hereinabove. These modifications and variations will not depart from the scope of the invention if defined by the following claims:

What is claimed is:

1. A diaphragm or pessary comprising a flexible wall having a shape adapted for accommodation in a vaginal cavity and for capping the cervical os in said cavity, said wall having an at least generally convex outer surface, and means in the form of projections distributed on said surface generally therethroughout for providing a texture simulating the natural vaginal mucosa.

2. A diaphragm or pessary as claimed in claim 1, wherein said wall has a center and said texture is formed at least generally symmetrically about said center in a polar sense.

3. A diaphragm or pessary as claimed in claim 2, wherein said texture includes discrete projections.

4. A diaphragm or pessary as claimed in claim 3, wherein the discrete projections are generally conical in shape.

5. A diaphragm or pessary as claimed in claim 2, wherein the texture is formed of at least generally concentric and circular ridges.

6. A diaphragm or pessary as claimed in claim 5, wherein said ridges are formed solely in said outer surface.

7. A diaphragm or pessary as claimed in claim 5, wherein said ridges are formed both in said outer surface and in an inner surface included by said wall.

8. A diaphragm or pessary as claimed in claim 5, further comprising a resilient annular ring encircling and connected to said wall.

9. A diaphragm or pessary as claimed in claim 5, wherein said ridges are of uniform width and height.

10. A diaphragm or pessary as claimed in claim 5, wherein said ridges are of irregular width.

11. A diaphragm or pessary as claimed in claim 5, wherein said ridges are of irregular height.

12. A diaphragm or pessary as claimed in claim 5, wherein said ridges have a height within a range of from about $\frac{1}{2}$ to $2\frac{1}{2}$ mm.

13. A diaphragm or pessary as claimed in claim 5, wherein said ridges have a width within a range of from about $\frac{1}{2}$ to $2\frac{1}{2}$ mm.

14. A diaphragm or pessary as claimed in claim 5, wherein said ridges are spaced circles.

15. A diaphragm or pessary as claimed in claim 5, wherein said ridges are continuous.

16. A diaphragm or pessary as claimed in claim 5, wherein said ridges are discontinuous.

17. A method comprising improving the utility of a diaphragm or pessary having an outer convex surface by texturizing said surface, at least generally throughout the same, by forming projections on said surface simulating the natural vaginal mucosa.

18. A method as claimed in claim 17, wherein said surface is texturized symmetrically in a polar sense.

19. A method as claimed in claim 18, wherein the surface is texturized by molding therein discrete projections.

20. A method as claimed in claim 18, wherein the surface is texturized by molding therein a concentric arrangement of ridges.

21. A method as claimed in claim 20, wherein the ridges are regular.

22. A method as claimed in claim 20, wherein the ridges are irregular.

* * * * *